United States Patent [19]

Petersen et al.

[11] Patent Number: 5,378,614
[45] Date of Patent: Jan. 3, 1995

[54] VECTOR AND METHOD FOR MAKING TISSUE FACTOR PATHWAY INHIBITOR (TFPI) ANALOGUES IN YEAST

[75] Inventors: Jens G. L. Petersen, Valby; Ole J. Nordfang, Hilleroed, both of Denmark

[73] Assignee: Novo Nordisk A/S, Bagsvaerd, Denmark

[21] Appl. No.: 26,145

[22] Filed: Mar. 2, 1993

Related U.S. Application Data

[63] Continuation-in-part of Ser. No. 828,920, Jan. 27, 1992, Pat. No. 5,312,736.

[30] Foreign Application Priority Data

Aug. 18, 1989 [DK] Denmark ................. 4080/89

[51] Int. Cl.$^6$ .................. C12N 1/19; C12N 15/81
[52] U.S. Cl. .................... 435/69.8; 435/69.2; 435/320.1; 435/254.2
[58] Field of Search ............ 435/69.6, 69.9, 320.1, 435/240.2, 69.2, 69.8; 530/395; 514/8

[56] References Cited

U.S. PATENT DOCUMENTS

| | | | |
|---|---|---|---|
| 4,977,092 | 11/1990 | Bitter | 435/320 |
| 5,024,941 | 6/1991 | Maine et al. | 435/69.9 |
| 5,106,833 | 4/1992 | Broze, Jr. et al. | 514/12 |
| 5,212,091 | 5/1993 | Diaz-Collier et al. | 435/69.6 |
| 5,312,736 | 5/1994 | Rasmussen et al. | 435/69.2 |

FOREIGN PATENT DOCUMENTS

| | | |
|---|---|---|
| 0300988 | 1/1989 | European Pat. Off. |
| 0318451 | 5/1989 | European Pat. Off. |
| WO90/08158 | 7/1990 | WIPO |

OTHER PUBLICATIONS

Girard et al., Nature, vol. 338, pp. 518–520 (1989).
Warn-Cramer et al., Thrombosis Research, vol. 48, pp. 11–22 (1987).
Broze, Jr. et al., Proc. Natl. Acad. Sci. USA, vol. 84, pp. 1886–1890 (187).
Wun et al., J. Biol. Chem., vol. 263, No. 13, pp. 6001–6004 (1988).
Stanley, P. (1992) Glycobiology 2(2): 99–107.

*Primary Examiner*—Garnette D. Draper
*Assistant Examiner*—David L. Fitzgerald
*Attorney, Agent, or Firm*—Steve T. Zelson; Karen A. Lowney

[57] ABSTRACT

A method for making TFPI analogues lacking part of the C-terminal end of the native TFPI molecule is described by cultivation of a yeast strain transformed with an expression vector containing a DNA sequence encoding such TFPI analogues. The TFPI analogues will at least contain the two first Kunitz domains and lack the third Kunitz domain.

8 Claims, 6 Drawing Sheets

```
       SalI                                                        NheI
       GTCGACC ATG ATT TAC ACA ATG AAG AAA GTA CAT GCA CTT TGG GCT AGC           49
               Met Ile Tyr Thr Met Lys Lys Val His Ala Leu Trp Ala Ser
               -28         -25                 -20                 -15

GTA TGC CTG CTG CTT AAT CTT GCC CCT GCC CCT CTT AAT GCT GAT TCT           97
       Val Cys Leu Leu Leu Asn Leu Ala Pro Ala Pro Leu Asn Ala Asp Ser
                   -10                 -5                           1

SacI
       GAG GAA GAT GAA GAA CAC ACA ATT ATC ACA GAT ACG GAG CTC CCA CCA          145
       Glu Glu Asp Glu Glu His Thr Ile Ile Thr Asp Thr Glu Leu Pro Pro
                   5                   10                  15

ApaI
       CTG AAA CTT ATG CAT TCA TTT TGT GCA TTC AAG GCG GAT GAT GGG CCC          193
       Leu Lys Leu Met His Ser Phe Cys Ala Phe Lys Ala Asp Asp Gly Pro
               20                  25                  30

TGT AAA GCA ATC ATG AAA AGA TTT TTC TTC AAT ATT TTC ACT CGA CAG          241
       Cys Lys Ala Ile Met Lys Arg Phe Phe Phe Asn Ile Phe Thr Arg Gln
       35                  40                  45                  50

ClaI
       TGC GAA GAA TTT ATA TAT GGG GGA TGT GAA GGA AAT CAG AAT CGA TTT          289
       Cys Glu Glu Phe Ile Tyr Gly Gly Cys Glu Gly Asn Gln Asn Arg Phe
                       55                  60                  65

GAA AGT CTG GAA GAG TGC AAA AAA ATG TGT ACA AGA GAT AAT GCA AAC          337
       Glu Ser Leu Glu Glu Cys Lys Lys Met Cys Thr Arg Asp Asn Ala Asn
                   70                  75                  80

AGG ATT ATA AAG ACA ACA CTG CAG CAA GAA AAG CCA GAT TTC TGC TTT          385
       Arg Ile Ile Lys Thr Thr Leu Gln Gln Glu Lys Pro Asp Phe Cys Phe
                   85                  90                  95

BamHI
       TTG GAA GAG GAT CCT GGA ATA TGT CGA GGT TAT ATT ACC AGG TAT TTT          433
       Leu Glu Glu Asp Pro Gly Ile Cys Arg Gly Tyr Ile Thr Arg Tyr Phe
                   100                 105                 110

ΔStuI
       TAT AAC AAT CAG ACA AAA CAG TGT GAA AGG TTC AAG TAT GGT GGA TGC          481
       Tyr Asn Asn Gln Thr Lys Gln Cys Glu Arg Phe Lys Tyr Gly Gly Cys
       115                 120                 125                 130

XhoI
       CTG GGC AAT ATG AAC AAT TTT GAG ACA CTC GAG GAA TGC AAG AAC ATT          529
       Leu Gly Asn Met Asn Asn Phe Glu Thr Leu Glu Glu Cys Lys Asn Ile
                       135                 140                 145
```

*FIG. 1A*

```
                                                            KpnI
TGT GAA GAT GGT CCG AAT GGT TTC CAG GTG GAT AAT TAT GGT ACC CAG        577
Cys Glu Asp Gly Pro Asn Gly Phe Gln Val Asp Asn Tyr Gly Thr Gln
            150                 155                 160

HpaI
CTC AAT GCT GTT AAC AAC TCC CTG ACT CCG CAA TCA ACC AAG GTT CCC        625
Leu Asn Ala Val Asn Asn Ser Leu Thr Pro Gln Ser Thr Lys Val Pro
            165                 170                 175

EcoRI
AGC CTT TTT GAA TTC CAC GGT CCC TCA TGG TGT CTC ACT CCA GCA GAT        673
Ser Leu Phe Glu Phe His Gly Pro Ser Trp Cys Leu Thr Pro Ala Asp
    180                 185                 190

ΔEcoRV
AGA GGA TTG TGT CGT GCC AAT GAG AAC AGA TTC TAC TAC AAT TCA GTC        721
Arg Gly Leu Cys Arg Ala Asn Glu Asn Arg Phe Tyr Tyr Asn Ser Val
195                 200                 205                 210

BspMII
ATT GGG AAA TGC CGC CCA TTT AAG TAC TCC GGA TGT GGG GGA AAT GAA        769
Ile Gly Lys Cys Arg Pro Phe Lys Tyr Ser Gly Cys Gly Gly Asn Glu
                215                 220                 225

SpeI                            SphI
AAC AAT TTT ACT AGT AAA CAA GAA TGT CTG AGG GCA TGC AAA AAA GGT        817
Asn Asn Phe Thr Ser Lys Gln Glu Cys Leu Arg Ala Cys Lys Lys Gly
            230                 235                 240

StuI
TTC ATC CAA AGA ATA TCA AAA GGA GGC CTA ATT AAA ACC AAA AGA AAA        865
Phe Ile Gln Arg Ile Ser Lys Gly Gly Leu Ile Lys Thr Lys Arg Lys
            245                 250                 255

AGA AAG AAG CAG AGA GTG AAA ATA GCA TAT GAA GAA ATT TTT GTT AAA        913
Arg Lys Lys Gln Arg Val Lys Ile Ala Tyr Glu Glu Ile Phe Val Lys
            260                 265                 270

SalI
AAT ATG TGAGTCGAC                                                      928
Asn Met
275
```

FIG. 1B

PP<sub>HSA</sub>-TFPI:

```
ATG AAG TGG GTT ACT TTC ATC TCT TTG TTG TTC TTG TTC TCT TCT GCT        48
Met Lys Trp Val Thr Phe Ile Ser Leu Leu Phe Leu Phe Ser Ser Ala
 1           5                  10                  15
<-               prepeptide of HSA XbaI
TAC TCT AGA GGT GTT TTC AGG AGG GAT TCT GAG                            81
Tyr Ser Arg Gly Val Phe Arg Arg Asp Ser Glu
            20                  25
    -> <-                  -> <-
     ↑                       ↑    TFPI
    signal peptidase        Kex2
```

212spx3-TFPI:

```
EcoRI
GAATTCATTC AAGAATAGTT CAAACAAGAA GATTACAAAC TATCAATTTC ATACACAATA      60

TAAACGATTA AAAGA ATG AAG GCT GTT TTC TTG GTT TTG TCC TTG ATC GGA       111
                Met Lys Ala Val Phe Leu Val Leu Ser Leu Ile Gly
                 1           5                  10
                <-         modified α-amylase signal peptide ApaI
TTC TGC TGG GCC CAA CCA GTC ACT GGC GAT GAA TCA TCT GTT GAG ATT        159
Phe Cys Trp Ala Gln Pro Val Thr Gly Asp Glu Ser Ser Val Glu Ile
         15                  20                  25
            ->    <-                   synthetic leader
             ↑
            signal peptidase CCG GAA GAG TCT CTG ATC ATC GCT GAA AAC ACC ACT TTG GCT AAC GTC        207
Pro Glu Glu Ser Leu Ile Ile Ala Glu Asn Thr Thr Leu Ala Asn Val
        30                  35                  40

NcoI
GCC ATG GCT AAG AGA GAT TCT GAG                                        231
Ala Met Ala Lys Arg Asp Ser Glu
 45             50
            -> <-
             ↑    TFPI
            Kex2
```

VECTOR AND METHOD FOR MAKING TISSUE FACTOR PATHWAY INHIBITOR (TFPI) ANALOGUES IN YEAST

CROSS REFERENCE TO RELATED APPLICATION

This application is a continuation-in-part of U.S. Ser. No. 07/828,920, filed Jan. 27, 1992, now U.S. Pat. No. 5,312,126.

FIELD OF THE INVENTION

The present invention relates to a method of producing tissue factor pathway inhibitor (TFPI) analogues in yeast.

BACKGROUND OF THE INVENTION

Blood coagulation is a complex process involving many activating and inactivating coagulation factors. Anticoagulant proteins are known to be important for regulation of the coagulation process and anticoagulants are thus important in the treatment of a variety of diseases, e.g. thrombosis, myocardial infarction, disseminated intravascular coagulation etc.

Thus heparin is used clinically to increase the activity of antithrombin III and heparin cofactor II. Antithrombin III is used for the inhibition of factor Xa and thrombin. Hirudin is used for the inhibition of thrombin and protein C may be used for the inhibition of factor V and factor VIII. Anticoagulant proteins may also be used in the treatment of cancer.

Coagulation can be initiated through the extrinsic pathway by the exposure of tissue factor (TF) to the circulating blood (Y. Nemerson, Blood 71 (1988) 1-8). Tissue factor is a protein cofactor for factor VII/VIIa and binding of tissue factor enhances the enzymatic activity of factor VIIa (FVIIa) towards its substrates factor IX and factor X.

Recently a new anticoagulant protein, the tissue factor pathway inhibitor (TFPI) has been isolated (G. J. Broze et al., Proc. Natl. Acad. Sci. 84 (1987) 1886-1890).

On a molar basis TFPI has been shown to be a potent inhibitor of TF/FVIIa-induced coagulation (R. A. Gramzinski et al., Blood 73 (1989) 983-989). TFPI binds and inhibits factor Xa (FXa) and the complex between TFPI and FXa inhibits TF/FVIIa (Rapaport, Blood 73 (1989) 359-365). TFPI is especially interesting as an anticoagulant/antimetastatic agent as many tumor cells express TF activity (T. Sakai et al., J. Biol. Chem. 264 (1989), 9980-9988) and because TFPI shows anti-Xa activity like antistatin which has antimetastatic properties.

Figure 1B:
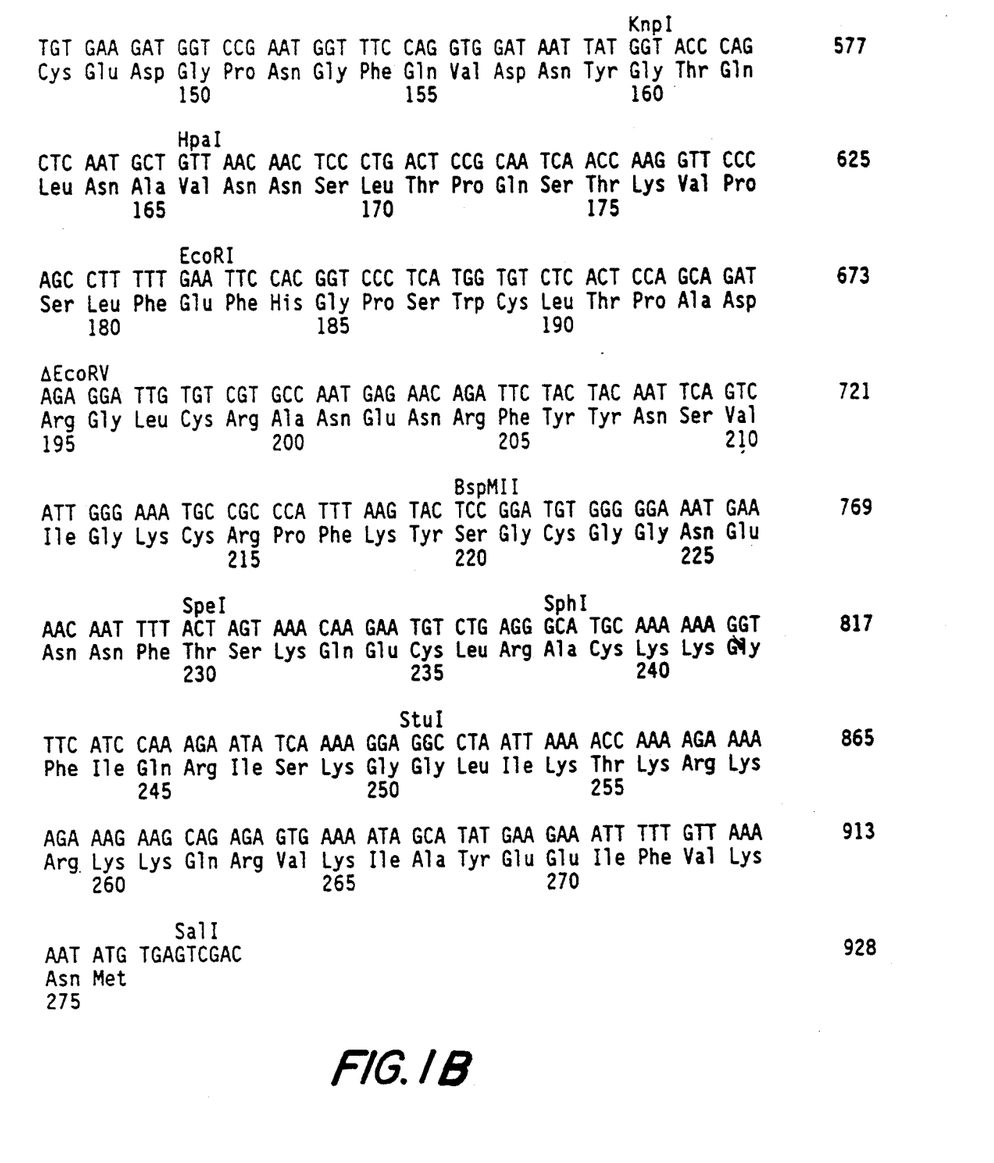

TFPI has been recovered by Broze et al. (supra) from HepG2 hepatoma cells (Broze EP A 300988) and the gene for the protein has been cloned (Broze EP A 318451). A schematic diagram over the secondary structure of TFPI is shown in U.S. Pat. No. 5,312,736 (WO 91/01253). The amino acid sequence of TFPI with its natural 28 amino acid signal peptide (Sequence ID Number 1 and 2) is shown in FIG. 1 where the N-terminal amino acid Asp is given the number 1. The protein consists of 276 amino acid residues and has in addition to three inhibitor domains of the Kunitz type, three potential glycosylation sites at position Asn117, Asn167 and Asn228. The molecular weight shows that some of these sites are glycosylated. Furthermore, it has been shown that the second Kunitz domain binds FXa while the first Kunitz domain binds FVIIa/TF (T. J. Girard et al., Nature 338 (1989) 518-520). TFPI has also been isolated from HeLa cells (PCT/DK90/00016) and it was shown that HeLa TFPI binds heparin.

In U.S. Pat. No. 5,312,736 certain TFPI analogues are described retaining the TFPI activity as well as anti Xa activity although parts of the molecule have been deleted. Furthermore, these analogues show a much lower affinity for heparin than full length TFPI, making them more useful as therapeutic agents than the native molecule. The TFPI analogues will furthermore have a longer half life as compared with native TFPI which will further reduce the amount of active ingredients for the medical treatment.

These TFPI analogues are thus characterized in having TFPI activity but with no or low heparin binding capacity under physiological conditions (pH, ionic strength).

In the present context the term "low heparin binding capacity" is intended to mean a binding capacity of about 50%, more preferably of about 25% and most preferably less than about 10% of that of native TFPI at physiological pH and ionic strength.

It was thus shown that the heparin binding capacity is lost when the sequence from amino acid residue number 162 to amino acid residue number 276 is deleted from the TFPI molecule. It was therefore concluded that the heparin binding domain is situated in this part of the TFPI molecule and it was assumed that the heparin binding domain comprises at least a region from Arg246 to Lys265 near the C-terminal end of the TFPI molecule being rich in positively charged amino acid residues.

The present invention is based on the surprising fact that active TFPI analogues lacking C-terminal parts of the molecule are expressed in good yields in yeast. This is the more surprising because attempts to express native TFPI in yeast gave only neglible amounts.

BRIEF DESCRIPTION OF THE INVENTION

In its broadest aspect, the present invention is related to a method of making TFPI analogues in yeast, said TFPI analogues containing at least the first and second Kunitz domain and lacking part of the C-terminal end of the native TFPI molecule by cultivation of a yeast strain transformed with an expression vector containing a DNA-sequence encoding such TFPI analogues in a suitable nutrient medium under conditions which are conductive to the expression of the TFPI.

In a more narrow aspect the present invention is related to a method of making TFPI analogues in yeast, said TFPI analogues containing at least the first and second Kunitz domain and lacking the third Kunitz domain from amino acid Cys189 to amino acid Cys239 as well as a substantial part of the amino acid sequence from Lys240 to Met276. With "a substantial part" is meant from about 70% to 100%. Preferably the TFPI analogues will lack the sequence from at least Cys189 to Lys265. The TFPI analogues may furthermore lack part of the amino acid sequence from amino acid Cys147 to Trp188 and part of the N-terminal sequence of native TFPI such as the sequence from amino acid residue 1 to 24.

The TFPI analogues may also contain a Ser residue as the N-terminal residue for efficient cleavage of a signal peptide by a signal peptidase. Thus, the N-terminal in the TFPI molecule may be replaced by a Ser or an additional Ser may be inserted adjacent to the original N-terminal residue.

The TFPI analogues may furthermore contain a modification of the potential N-glycosylation triade Asn117, Gln118, Thr119 to avoid glycosylation. Such modification will include a mutation and/or a deletion of one or more of the amino acid residues Asn117, Gln118, Thr119; see copending patent application Ser. No. 08/026,146. Asn117 may thus be replaced by Gln which cannot be glycosylated.

The present invention is thus related to a method of expressing TFPI analogues in yeast, said TFPI analogues containing at least the amino acid sequence from Phe25 to Glu148 of the native TFPI molecule and lacking the third Kunitz domain from amino acid Cys189 to amino acid Cys239 and a substantial part of the amino acid sequence from Lys240 to Met276 of the native TFPI molecule.

In a more preferred embodiment, the present invention is related to a method of expressing TFPI analogues in yeast, said TFPI analogues containing the amino acid sequence from Asp1 to Glu148 of the native TFPI molecule and lacking the third Kunitz domain from Cys189 to Cys239 and furthermore lacking a substantial part of the amino acid sequence from Lys240 to Met276 of the native TFPI molecule.

In an even more preferred embodiment the present invention is related to a method of making TFPI analogues in yeast, said TFPI analogues lacking the amino acid sequence from Gln162 to Met276 of the native TFPI molecule in yeast.

In a further aspect, the present invention is related to a recombinant yeast expression vector which comprises DNA sequences encoding functions facilitating gene expression, including a promoter and a terminator, linked functionally to a DNA sequence encoding the TFPI analogues and capable of expressing the TFPI analogues in yeast.

In a still further aspect, the present invention is related to a yeast strain containing a recombinant yeast expression vector as defined above.

DETAILED DESCRIPTION OF THE INVENTION

The cDNA for the native TFPI has been cloned and sequenced (T. C. Wun et al., J. Biol. Chem. 263 (1988) 6001-6004). DNA sequences encoding the desired TFPI analogue may be constructed by altering TFPI cDNA by site-directed mutagenesis using synthetic oligonucleotides encoding the desired amino acid sequence in accordance with well-known procedures.

The DNA sequence encoding the TFPI analogue of the invention may also be prepared synthetically by established standard methods. Thus oligonucleotides may be synthesized, by phosphoamidite chemistry in an automatic DNA synthesizer, purified, annealed, ligated and cloned in suitable vectors.

The yeast expression vector according to the invention may be any vector which may conveniently be subjected to recombinant DNA procedures, and which is capable of expressing the gene for the TFPI analogues in yeast. Thus, the vector may be an autonomously replicating vector, i.e. a vector which exists as an extrachromosomal entity, e.g. a plasmid. Alternatively, the vector may be one which, when introduced into a host cell, is integrated into the host cell genome and replicated together with the chromosome(s) into which it has been integrated.

In the expression vector, the DNA sequence encoding the TFPI analogue will be operably connected to a suitable promoter sequence. The promoter may be any DNA sequence which shows transcriptional activity in the yeast host cell of choice and may be derived from genes encoding proteins either homologous or heterologous to the yeast host cell. Suitable yeast promoters include promoters from yeast glycolytic genes (R. A. Hitzeman et al., J.Biol.Chem. 255 (1980) 12073-12080; T. Alber and G. Kawasaki, J.Mol.Appl.Gen. 1 (1982) 419-434) or alcohol dehydrogenase genes (T. Young et al., in Genetic Engineering of Microorganisms for Chemicals (Hollaender et al., eds.), Plenum Press, New York, 1982 pp. 335-361) or other highly expressed genes. Specific examples are the TPI1 (T. Alber and G. Kawasaki, op. cit., U.S. Pat. No. 4,599,311) or the ILV5 (J. G. L. Petersen and S. Holmberg, Nucl. Acids Res. 14 (1986) 9631-9651) promoter.

The DNA sequence encoding the TFPI analogues should also be operably connected to a suitable terminator sequence which show transcription termination activity in yeast. Such terminator sequences may be derived from the 3' untranslated regions of yeast genes such as TPI1 (Alber and Kawasaki, op. cit.) and ILV5 (J. G. L. Petersen and S. Holmberg, op. cit.). The vector may further comprise elements such as polyadenylation signals, transcriptional enhancer sequences and translational enhancer sequences.

Within the present invention it is preferred to express TFPI analogues in yeast host cells that can secrete the analogues into the culture media. To direct the TFPI analogues into the secretory pathway of the yeast host cell, a secretory signal sequence is operably linked to the TFPI analogue DNA sequence. The secretory signal should preferably be cleaved in vivo, e.g. by a signal peptidase or by the yeast KEX2 protease (D. Julius et al., Cell 37 (1984) 1075-1089) during export of the fusion protein to allow for secretion of the TFPI analogue having the correct N-terminal amino acid. Suitable secretory signals include the alpha factor signal sequence (J. Kurjan and I. Herskowitz, Cell 30 (1982) 933-943, U.S. Pat. No. 4,546,082 and EP 116,201), the PH05 signal peptide (WO 86/00637), secretory signal sequences derived from the BAR1 gene (U.S. Pat. No. 4,613,572 and WO 87/002670), the SUC2 signal peptide (M. Carlson et al., Mol. Cell. Biol. 3 (1983) 439-447) and the human serum albumin prepropeptide (A. Dugaiczyk et al., Proc. Natl. Acad. Sci. USA, 79 (1982) 71-75). Alternatively, a secretory signal sequence may be synthesized according to the rules established, for example, by G. von Heinje (Nucl. Acids Res. 14 (1986) 4683-4690). Examples of synthetic secretory signal sequences are described in WO 89/02463 and WO 92/13065.

Suitable yeast vectors for use in the present invention include YRp7 (K. Struhl et al., Proc. Natl. Acad Sci. USA 76 (1987) 1045-1039), YEp13 (J. R. Broach et al., Gene 8 (1979) 121-133), POT vectors (U.S. Pat. No. 4,931,373), pJDB249 and pJDB219 (J. Beggs, Nature 275 (1978) 104-109) and derivatives thereof. Such vectors will generally include a selectable marker, which may be one of any number of genes that exhibit a dominant phenotype for which a phenotypic assay exists to enable transformants to be selected. Preferred selectable markers are those that complement host cell auxotrophy, provide antibiotic resistance or enable a cell to utilize specific carbon sources, and include LEU2 (Broach et al., op.cit.), URA3 (Botstein et al., Gene 8

(1979) 17), HIS3 (Struhl et al., op.cit.) or POT1 (U.S. Pat. No. 4,931,373).

Techniques for transforming yeast are well known in the literature, and have been described for instance by Beggs (op.cit.). The genotype of the host cell will generally contain a genetic defect that is complemented by the selectable marker present on the expression vector. Choice of a particular host and selectable marker is well within the level of ordinary skill in the art. To optimize production of heterologous proteins, it is preferred that the host strain carry a mutation, such as the yeast pep4 mutation (E. W. Jones, Genetics 85 (1977) 23–33), which results in reduced proteolytic activity.

The recombinant expression vector of the invention may further comprise a DNA sequence enabling the vector to replicate in the host cell in question. An example of such a sequence is the yeast 2-micron sequence.

The procedures used to ligate the DNA sequences coding for the TFPI analogue of the invention, the promoter and the terminator, respectively, and to insert them into suitable vectors containing the information necessary for replication, are well known to persons skilled in the art.

The yeast host cell may be any yeast species which is capable of producing the TFPI analogue. Examples of suitable yeast host cells include strains of Saccharomyces spp., Schizosaccharomyces spp. Kluyveromyces spp., Pichia spp. and Hansenula spp., in particular strains of *Saccharomyces cerevisiae*.

The transformed yeast cells are grown according to standard methods in a growth medium containing nutrients required for growth of the particular yeast host cells. A variety of suitable media are known in the art and generally include a carbon source, a nitrogen source, essential amino acids, vitamins, minerals and growth factors. The growth medium will generally select for cells containing the DNA construct by, for example, drug selection or deficiency in an essential nutrient which is complemented by the selectable marker on the DNA construct or co-transfected with the DNA construct.

Suitable growth conditions for yeast cells, for example, include culturing in a medium comprising a nitrogen source (e.g. yeast extract or nitrogen-containing salts), inorganic salts, vitamins and essential amino acid supplements as necessary at a temperature between 4° C. and 37° C., with 30° C. being particularly preferred. The pH of the medium is preferably maintained at a pH greater than 2 and less than 8, more preferably pH 5–6.

The TFPI analogue will preferably be secreted to the growth medium and may be recovered from the medium by conventional procedures including separating the host cells from the medium by centrifugation or filtration, precipitating the proteinaceous components of the supernatant or filtrate by means of a salt, e.g. ammonium sulphate, followed by purification by a variety of chromatographic procedures, e.g. ion exchange chromatography, affinity chromatography, or the like.

The novel TFPI analogues may be used for the treatment of patients having coagulation disorders or cancer; see U.S. Pat. No. 5,312,736.

BRIEF DESCRIPTION OF THE DRAWINGS

The present invention is further described with reference to the drawings in which FIG. 1A and 1B together show a synthetic gene for human TFPI including the signal peptide and the corresponding amino acid sequence.

The invention is further described in the following examples which are not in any ways intended to limit the scope or spirit of the invention as claimed.

Experimental Part

Materials and Methods

Standard recombinant DNA techniques were carried out as described (T. Maniatis et al., Molecular Cloning. A Laboratory Manual. Cold Spring Harbor Laboratory, 1982).

Synthetic oligonucleotides were synthesized by the phosphoramidite method using an Applied Biosystems DNA Synthesizer Model 380B.

Restriction endonucleases and T4 DNA ligase were obtained from New England Biolabs. Modified T7 DNA polymerase (Sequenase) was obtained from United States Biochemicals. Restriction endonucleases and other enzymes were used in accordance with the manufacturers recommendations. pBS+ (Stratagene) was used as cloning vector for construction of the synthetic TFPI gene by cloning of synthetic DNA fragments.

*E. coli* strains XL-1 Blue (Stratagene) and MC1061 (M. J. Casadaban and S. N. Cohen, J. Mol. Biol. 138 (1980) 179–207) were used as bacterial recipients for plasmid transformations and as hosts for propagation and preparation of plasmid DNA.

Strains of *Saccharomyces cerevisiae* used as hosts for expression of TFPI analogues were the two diploids E18 (MATa/MATα Δtpi::LEU2/Δtpi::LEU2 leu2/-leu2 +/his4 pep4–3/pep4–3) (U.S. Pat. No. 4,931,373) and YNG452 (MATα/MATα ura3-52/ura3-52 leu2-Δ2/leu2-Δ2 +/his4 pep4-Δ1/pep4-Δ1). The latter was derived from strain JC482 (J. F. Cannon and K. Tatchell, Mol. Cell. Biol. 7 (1987) 2653–2663).

Yeast expression vectors used for expression of TFPI analogues in yeast were of the POT-type (US Patent No. 4,931,373) or the URA3-LEU2d-2μ plasmid pAB24 (P. J. Barr et al., in Proc. Alko Symp. on Industrial Yeast Genetics (Korkola and Nevalainen, eds.) Found. Biotech. Industr. Ferment. Res. 5 (1987) 139–148).

DNA sequences were determined by the dideoxy chain termination method (Sanger et al., Proc. Natl. Acad. Sci. 74 (1977) 5463–5467) using double stranded plasmid DNA as template and $^{32}$P- or $^{35}$S labelled primers and Sequenase.

Western blot analysis was carried out as described by J. Mikkelsen and J. Knudsen (Biochem. J. 248 (1987) 709–714).

Affinity purification of the TFPI analogues was carried out from culture supernatants by affinity chromatography using polyclonal anti-TFPI immunoglobulin G coupled to Sepharose (O. Nordfang et al., Biochemistry 30 (1991) 10371–10376).

TFPI activity was measured in a chromogenic microplate assay, modified after the method of Sandset et al., (Thromb. Res. 47 (1987), 389–400). Heat treated plasma pool was used as a standard. This standard is defined as containing 1 U/ml of TFPI activity. Standards and samples were diluted in buffer A (0.05M Tris-HCl, 0.1M NaCl, 0.1M Na-citrate, 0.02% NAN$_3$, pH 8.0) containing 2 μg/ml polybrene and 0.2% bovine serum albumin. FVIIa/TF/FX/CaCl$_2$ combination reagent was prepared in buffer A and contained 1.6 ng/ml FVIIa (Novo Nordisk A/S), human tissue factor diluted 60 fold, 50 ng/ml FX (Sigma) and 18 mM CaCl$_2$. The assay was performed in microplate strips at 37° C. 50 μl of samples and standards were pipetted into the strips and 100 μl combination reagent was added to each well. After 10 minutes incubation, 25 μl of FX (3.2 μg/ml) was added to each well and after another 10 minutes 25 μl of chromogenic substrate for FXa (S2222) was added 10 minutes after the addition of substrate. The reaction was stopped by addition of 50 μl 1.0M citric acid pH 3.0. The microplate was read at 405 nm.

The inhibitory activity of TFPI analogues in the extrinsic pathway of coagulation was measured in PT clotting assay using human plasma and diluted human thromboplastin (O. Nordfang et al., op.cit.).

EXAMPLE 1

Construction of genes encoding TFPI analogues for secretion in yeast

In U.S. Pat. No. 5,312,736, a synthetic gene for human TFPI with its 28 amino acid signal peptide was described. The DNA sequence was derived from the published sequence of a cDNA coding for human TFPI (Wun et al., J. Biol. Chem. 263 (1988) 6001–6004). The synthetic gene was assembled by the step-wise cloning of synthetic restriction fragments into plasmid pBS(+). The resulting gene was contained on a 922 base pair (bp) SalI restriction fragment. The gene had 26 silent nucleotide substitutions in degenerate codons as compared to the cDNA resulting in fourteen unique restriction endonuclease sites in order to facilitate the introduction of mutations in TFPI as well as the in-frame insertion of new secretion signals at the N-terminal of mature TFPI. The DNA sequence of the 922 bp SalI fragment and the corresponding amino acid sequence of human TFPI (pre-form) is shown in FIG. 1.

Using standard DNA manipulation technology, the coding sequences for TFPI analogues were constructed from the synthetic TFPI gene by replacing portions of the TFPI gene with appropriate synthetic DNA fragment. The DNA fragments were annealed oligodeoxynucleotides synthesized by phosphoramidite chemistry. Resulting plasmids were propagated in E. coli and the nucleotide sequences verified by DNA sequencing. The exemplary TFPI analogues constructed in this manner were all characterized by lacking different portions of the C-terminal one third of the TFPI polypeptide, and thus retaining at least the first two Kunitz Domains. Some derivatives had an Asn to Gln substitution at the potential N-glycosylation site at position 117 (Wun et al. op.cit., T. J. Girard et al., Thromb. Res. 55 (1989) 37–50) by changing the codon AAT (Asn) to CAA (Gln)) in order to avoid the addition of N-linked oligosaccharides at this site during expression and secretion in yeast. The following TFPI polypeptides were expressed in yeast:

| Name | Characteristics | Polypeptide |
| --- | --- | --- |
| TFPI | full length | Asp1—Met276 |
| TFPI-117Gln | full length | Asp1—Met276(117Gln) |
| TFPI$_{1-252}$ | lacking the 24 C-terminal amino acids | Asp1—Leu252 |
| TFPI$_{1-161}$ | 2-domain | Asp1—Thr161 |
| TFPI$_{1-161}$-117Gln | 2-domain, lacking N-glycosylation sites | Asp1—Thr161(117Gln) |
| TFPIΔ3-117Gln | 2-domain, internal deletion of domain 3 retaining the C-terminal, lacking N-glycosylation sites | Asp1—Gly150/ Phe243—Met276— (117Gln) |

The TFPI polypeptides above were expressed in yeast in secretable forms by replacing the coding sequence for the 28 amino acid signal peptide of TFPI (FIG. 1A) with synthetic DNA fragments encoding two different heterologous secretion signals, namely the human serum albumin prepropeptide (pp$_{HSA}$) (A. Dugaiczyk et al., Proc. Natl. Acad. Sci. USA, 79 (1982) 71–75) and the synthetic secretion signal 212spx3 (WO 89/02463). The 212spx3 signal consists of the signal peptide of mouse salivary gland α-amylase with residues Ala3Val4 changed to Phe, and Val7 to Leu, followed by a synthetic leader sequence. Both signals provided at their C-termini a pair of basic amino acids fused to the N-terminal Asp1 of mature TFPI to allow for secretion of correctly processed TFPI by cleavage in vivo by the yeast KEX2 protease (D. Julius et al., Cell 37 (1984) 1075–1089).

Figure 2:
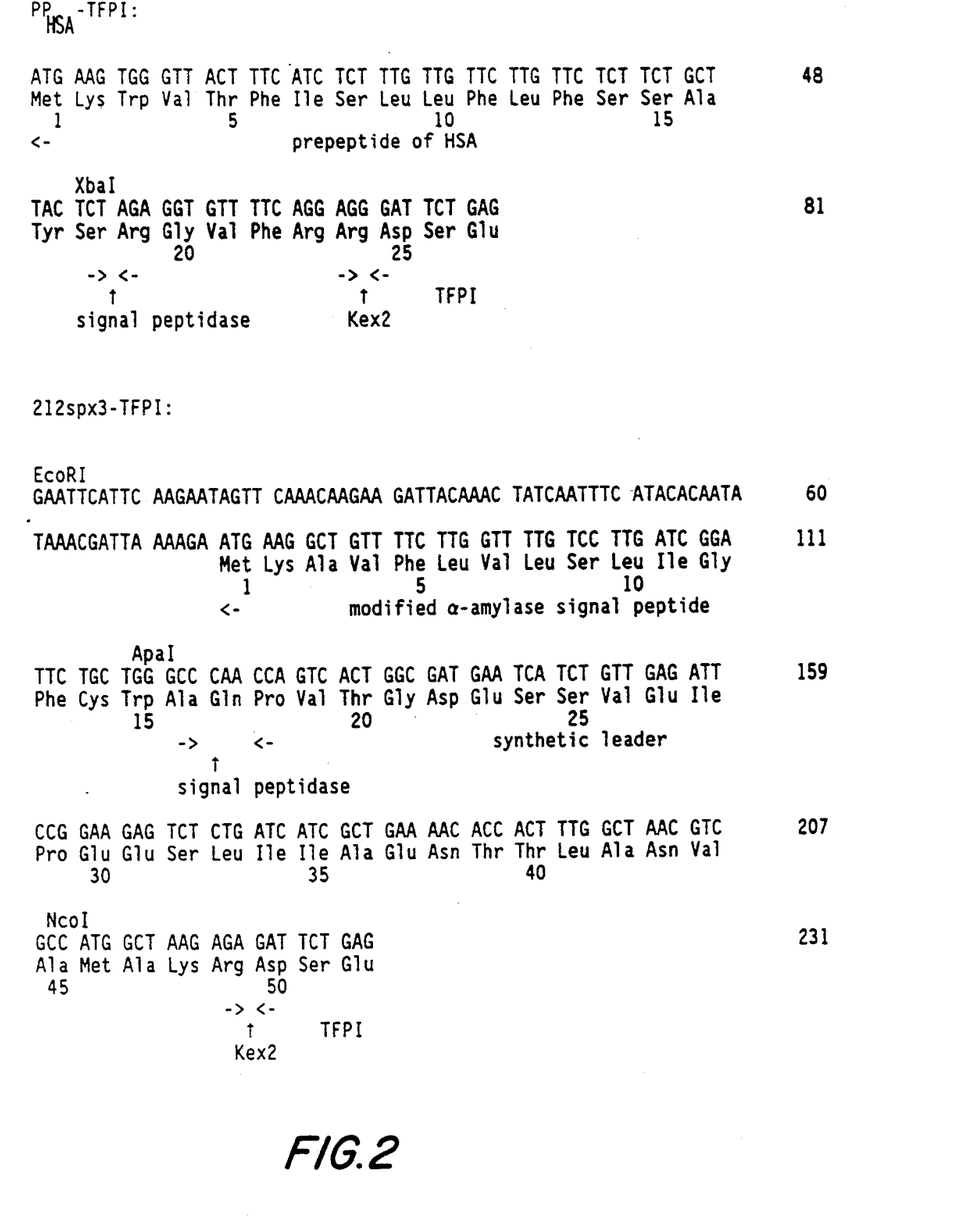
FIG. 2 shows DNA-sequences and corresponding amino acid sequences for the prepropeptide of human serum albumin ($pp_{HSA}$) (Sequence ID Number 3 and 4) and the synthetic secretion signal 212spx3 (Sequence ID Number 5 and 6) fused to the N-terminal of the mature form of TFPI. Only the three N-terminal amino acids of TFPI are shown.

The DNA sequences and translated amino acid sequences for the two secretion signals fused to TFPI are shown in FIG. 2.

EXAMPLE 2

Construction of yeast expression plasmids

In order to express the TFPI mutant forms in yeast, the genes were placed between a yeast promoter and a yeast terminator in yeast-E. coli vectors. In the present example, the strong constitutive promoters of the ILV5 (J. G. L. Petersen and S. Holmberg, Nucl. Acids Res. 14 (1986) 9631–9651) or TPI1 (T. Alber and G. Kawasaki, J. Mol. Appl. Genet. 1 (1982) 419–434) genes of S. cerevisiae were used. Transcription terminator sequences were derived from the same two genes. The ILV5 promoter fragment employed was from position −346 to −1 of the published sequence of ILV5 with a BamHI site added at the upstream end via a synthetic linker. The ATG translation start codon of the different signal-TFPI fusion genes were inserted at the putative start codon for the ILV5 gene. The ILV5 terminator fragment used was from position +1172 to +1823 of the published sequence with a SalI site at the upstream position and a poly-linker sequence downstream. The TPI promoter was from position −11 to −379 of the published sequence except that the SphI site in this fragment had been deleted. At the upstream end was added a SphI site, and at position −10 was added en EcoRI site, which could be conveniently used for the insertion of DNA fragments encoding 212spx3-TFPI fusions (see FIG. 2). The TPI1 terminator was from the XbaI site in the 3' end of the TPI1 coding region and 0.7 kb downstream where a BamHI site was inserted.

Figure 3:
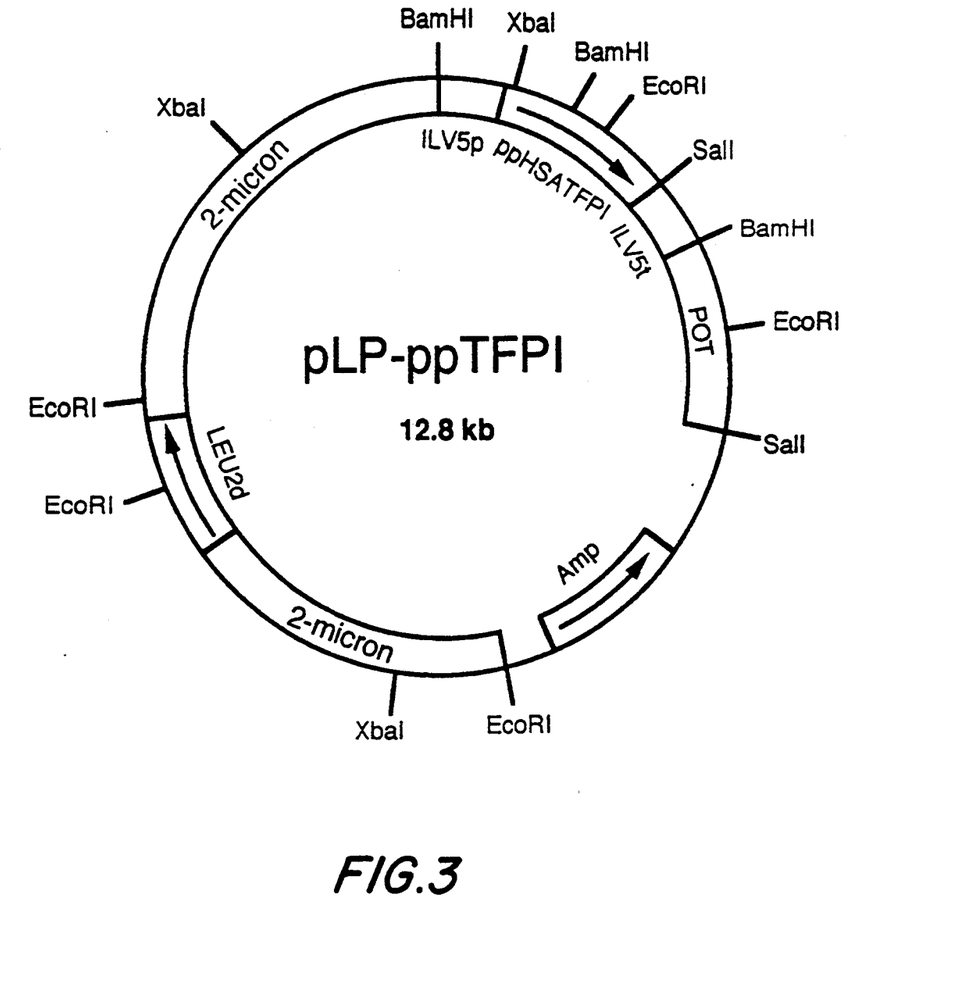
FIG. 3 shows a restriction site map of yeast POT-expression plasmid pLP-ppTFPI.

The TFPI expression cassettes thus constructed were inserted in yeast vectors. In the present example, we used the POT-type (pRPOT, similar to CPOT, U.S. Pat. No. 4,931,373) characterized by carrying the *Schizosaccharomyces pombe* triosephosphate isomerase gene (POT) (P. R. Russell, Gene 40 (1985) 125–130) as selectable marker for the purpose of plasmid stabilization in tpi1 mutants of *S. cerevisiae*. The plasmids contained most of the yeast 2-micron plasmid for replication in yeast, and pUC13 sequences for selection and maintenance in *E. coli*. The POT vector contained in some cases also the defective LEU2d gene derived from plasmid PJDB219 (J. Beggs, Nature 275 (1978) 104–109). This marker was not used for selection in this example. A representative plasmid construct is shown in FIG. 3.

Some TFPI analogues were also expressed from plasmid pAB24 (P. J. Barr et al., in Proc. Alko Symp. on Industr. Yeast Genet. Kornola and Nevalaiken, eds. Found. Biotech. Industr. Ferment. Res. 5 (1982) 139–148).

EXAMPLE 3

Production of TFPI analogues in yeast

The TFPI expression plasmids with the POT gene as selectable marker were introduced into the diploid *S. cerevisiae* strain E18. The host strain grows poorly on media with glucose as the carbon source due to the chromosomal deletion of the gene for triose phosphate isomerase. For transformation, the strain was grown in medium with glycerol and lactate as the carbon sources and spheroblasts prepared according to J. Beggs (op.-cit.). Transformants were selected in top-agar on minimal plates containing sorbitol and with glucose as the carbon source. In expression studies, reisolated transformants were grown in rich glucose medium (YPD) (F. Sherman, G. R. Fink and J. B. Hicks, Methods in Yeast Genetics, A Laboratory Manual. Cold Spring Harbor Laboratory, 1986) in shake flasks at 30° C. to stationary phase. Following centrifugation, cell pellets and media were stored at −20° C. until further analysis. Expression plasmids based on vector pAB24 were transformed into strain YNG452 selecting for uracil prototrophy on synthetic medium lacking uracil by the alkali cation transformation procedure (H. Ito et al., J. Bacteriol. 153 (1983) 163–168). Transformants of YNG452 were propagated in synthetic media without uracil.

The activity of TFPI was measured in media supernatants by the chromogenic FXa/TF/FVIIa-dependent two-stage assay. The results are summarized in Table I.

TABLE I

Levels of secreted TFPI from yeast transformants of strain E18 TFPI activity in the culture medium after three days of growth at 30° C. was determined relative to absorbance of the culture at 600 nm. Values are the mean of 2–10 independent experiments.

| Promoter | Secretion signal | TFPI/ TFPI analogue | Secreted TFPI activity (U/ml · $A_{600}$) |
|---|---|---|---|
| ILV5 | $PP_{HSA}$ | TFPI | 0.002 |
| TPI1 | 212spx3 | TFPI | 0.008 |
| TPI1 | 212spx3 | $TFPI_{1-252}$ | 0.004 |
| ILV5 | 212spx3 | TFPI-117Gln | 0.007 |
| ILV5 | $PP_{HSA}$ | $TFPI_{1-161}$ | 0.45 |
| TPI1 | 212spx3 | $TFPI_{1-161}$ | 4.9 |
| TPI1 | 212spx3 | $TFPI_{1-161}$-117Gln | 4.0 |
| TPI1 | 212spx3 | TFPIΔ3-117Gln | 0.10 |
| — | — | placebo | <0.002 |

As seen in Table I, plasmids for full length TFPI gave only low levels of activity in the culture medium with both secretion sequences. Full length TFPI with a substitution of one of the three potential sites for N-linked glycosylation (Asn117 to Gln) also showed very low levels of secretion.

Expressing of a TFPI variant, $TFPI_{1-252}$ lacking the C-terminal basic region of TFPI gave rise to about the same low levels of secreted activity as observed with full length TFPI.

Expression of TFPIΔ3–117Gln, which lacks the third Kunitz domain and potential N-glycosylation sites gave more than 10 times higher yields compared with full length TFPI.

About a 200-fold increase in secreted activity relative to the full length protein was observed when $TFPI_{1-161}$ was expressed in yeast using the ILV5 promoter and the prepropeptide of HSA. With the TPI1 promoter and signal sequence 212spx3, a further 10-fold increase was obtained. Substitution of the single potential N-glycosylation site in $TFPI_{1-161}$ (resulting in $TFPI_{1-161}$–117Gln) did not affect the level of secreted activity.

From these results it can be concluded that full length and near to full length TFPI containing the third Kunitz domain and a substantial part of the sequence from amino acid Lys240 to Met276 of native TFPI were expressed only poorly in yeast as measured by secreted activity, while surprisingly TFPI analogues lacking the third Kunitz domain and a substantial part of the sequence Lys240 to Met276 were secreted at significantly higher levels.

EXAMPLE 4

Anticoagulant properties of TFPI analogues from yeast

In order to measure the anticoagulant activities of TFPI and $TFPI_{1-161}$ secreted from yeast, the polypeptides were partly purified by affinity-chromatography using a polyclonal antibody towards TFPI coupled to Sepharose and their anticoagulant activity determined in traditional prothrombin time (PT) coagulation assays. Anticoagulant units were normalized to chromogenic TFPI activity which was assumed to be similar to the different TFPI forms. In this assay, TFPI in human plasma used as standard was defined to have a relative anticoagulant activity of 1. The results are shown in Table II. A relative anticoagulant activity of 0.18 was determined for full length TFPI produced in yeast. A comparable activity was found for TFPI with the Asn117 to Gln substitution. These activities are 5–9 times lower than for human, high-activity TFPI produced in BHK cells, but similar to C-terminally fragmented TFPI prepared as described by O. Nordfang et al. (Biochemistry 30 (1991) 10371–10376) and may be due to partial C-terminal fragmentation. In contrast, about 60-fold lower anticoagulant activities were observed for the two-domain polypeptides TFPI$_{1\text{-}161}$ and TFPI$_{1\text{-}161}$–117Gln as compared to intact TFPI from BHK cells.

TABLE II

Anticoagulant activity of TFPI variants
TFPI polypeptides secreted from yeast transformants were purified by affinity chromatography and their anticoagulant activity measured in a PT clotting assay relative to FXa/TF/FVIIa-dependent TFPI activity.

| TFPI molecule | TFPI activity (U/ml) | Anticoagulant activity (units/ml) | Relative anticoagulant activity |
|---|---|---|---|
| TFPI | 8.3 | 1.5 | 0.18 |
| TFPI-117Gln | 14.0 | 4.3 | 0.31 |
| TFPI$_{1\text{-}161}$ | 102.0 | 2.8 | 0.027 |
| TFPI$_{1\text{-}161}$-117Gln | 99.0 | 2.6 | 0.026 |
| From BHK cells: | | | |
| TFPI | 10.0 | 15.8 | 1.6 |
| Heterogenous C-term. | 100.0 | 10.9 | 0.11 |

EXAMPLE 5

Western analysis of secreted and intracellular TFPI and TFPI$_{1\text{-}161}$

Figure 4:
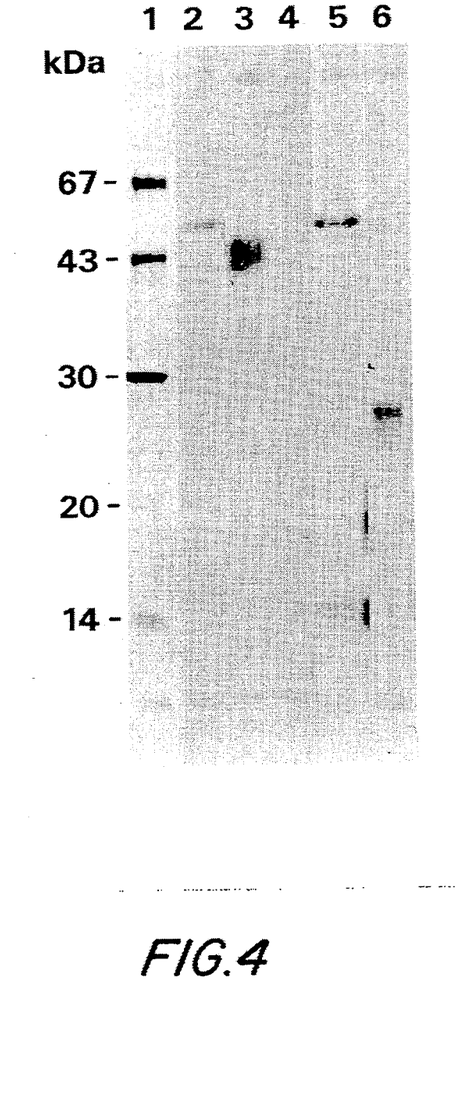
FIG. 4 shows a Western analysis of affinity-purified TFPI and $TFPI_{1-161}$ secreted from yeast transformants. Lane 1, Molecular weight markers, lanes 2 and 5, full length $TFPI_{1-276}$ (0.7 U per lane) secreted by yeast expressing $pp_{HSA}TFPI$; lane 3, TFPI secreted from a transfected BHK cell line (0.7 U) (A. H. Pedersen et al., J.Biol.Chem. 265 (1990) 16786–16793); lanes 4 and 6, $TFPI_{1-161}$ secreted by transformant expressing $pp_{HSA}TFPI_{1-161}$ (0.7 U). After electrophoresis and blotting onto nitrocellulose filter, immunodetection was performed with monoclonal antibodies, lanes 2–4 with an anti-C-terminal antibody (O. Nordfang et al., Biochemistry 30 (1991) 10371–10376) and lanes 5 and 6 with anti-N-terminal antibody (A. H. Pedersen et al., op.cit.)

The analysis of secreted TFPI and TFPI analogues in Table I depended on activity measurements of the culture medium, and did not necessarily reflect the molar amounts of polypeptides being secreted. Thus, the low levels of full length TFPI could be a result of mainly inactive product being secreted, e.g. as a result of proteolytic degradation or improper folding. Therefore, the expression of TFPI and TFPI$_{1\text{-}161}$ was analyzed by Western blotting using different antibodies towards TFPI (FIG. 4). The samples of supernatant media or cell extracts were partially purified by anti-TFPI affinity chromatography before SDS polyacrylamide gel electrophoresis and Western blot analysis. Expression of full length TFPI (lanes 2 and 5) gave rise to a predominant protein band with an apparent molecular mass of 50 kDa. The polypeptide reacted both with antibodies against the N- and C-terminal regions suggesting that the polypeptide was full length. The lower mobility as compared to TFPI expressed in transfected BHK cells (lane 3) suggested that more extensively glycosylation takes place in yeast. TFPI$_{1\text{-}161}$ reacted as expected only with the anti-N antibody (lanes 4 and 6). The major immunoreactive species appeared as a broad band of about 25 kDa.

Comparable staining intensities were obtained in Westerns with TFPI from yeast or BHK cells, and with TFPI$_{1\text{-}161}$ from yeast (FIG. 4). Since the same amounts of activity were analyzed (0.7 U per lane) it appears as the three preparations have similar specific activities.

A similar analysis by Western blotting was carried out with cell extracts of transformants expressing TFPI and TFPI$_{1\text{-}161}$ fused to the prepropeptide of HSA. The cell extract of the full length TFPI transformant upon partial immuno-affinity purification showed 2–3 bands of 34–39 kDa which could represent full length, underglycosylated TFPI, while the TFPI$_{1\text{-}161}$ transformant showed a major band of 25 kDa and a minor band of 22 kDa, probably representing glycosylated and unglycosylated TFPI$_{1\text{-}161}$, respectively.

Pilot-scale purification of TFPI$_{1\text{-}161}$

In order to obtain a large quantity of homogeneously pure TFPI$_{1\text{-}161}$, a yeast transformant expressing the analogue fused to the prepropeptide of HSA was propagated in a pilot-scale fermentor to high cell density. The resulting fermentation medium after removal of the cells by centrifugation contained about 650 U/ml of TFPI activity. The purification scheme for TFPI$_{1\text{-}161}$ from this batch is summarized in Table III. At each step, fractions with high TFPI activity and low protein content were pooled for further purification.

TABLE III

Purification of TFPI$_{1\text{-}161}$
Yeast transformants of strain YNG452 expressing TFP$_{1\text{-}161}$ fused to the prepropeptide of HSA was grown in a 2000 l fermentor and secreted TFPI$_{1\text{-}161}$ purified from the cleared supernatant medium.

| Purification step | Volume (l) | Total TFPI activity ($10^6$ U) | Yield % |
|---|---|---|---|
| Fermentation medium | 1050 | 680 | 100 |
| Cation exchange (pH 3.0) | 73 | 92 | 13 |
| FF-Q anion exchange (pH 9.3) | 7.8 | 73 | 11 |
| Freeze-drying and gel filtration on Superdex 75 (pH 3.4) | 1.2 | 78 | 11 |
| S-Sepharose cation exchange (pH 3.4) | 1.4 | 57 | 8 |
| Precipitation by isopropanol, dissolution in H$_2$O, freeze-drying | — | 49 | 7 |

About $5 \times 10^7$ U were isolated corresponding to a purification yield of about 7%. The rather low yield was mainly caused by loss of material during the first step of purification involving cation exchange chromatography.

Figure 5:
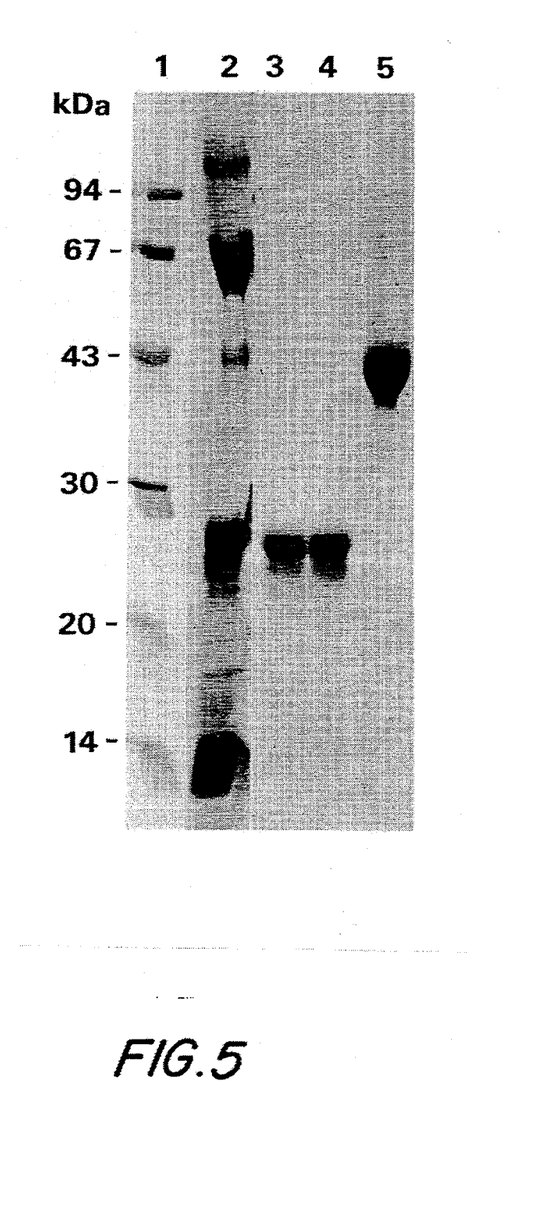
FIG. 5 shows an SDS polyacrylamide gel of purified $TFPI_{1-161}$. Lane 1, Molecular weight markers; Lane 2, $TFPI_{1-161}$ secreted to the growth medium in pilot-scale fermentor by a yeast transformant expressing $pp_{HSA}TFPI_{1-161}$ after initial ion exchange chromatography (200 U); lanes 3 and 4, two preparations of $TFPI_{1-161}$ upon further purification by gel filtration and cation exchange chromatography (200 U); lane 5, TFPI isolated from transfected BHK cell line (200 U). The proteins were stained with Coomassie Brilliant Blue R250.

SDS-PAGE analysis of the purified TFPI$_{1\text{-}161}$ showed a single protein band of 25 kDa after staining with Coomasie Brilliant Blue (FIG. 5, lanes 3 and 4). After the initial cation and anion exchange chromatography several additional polypeptides were present (lane 2). Among these, the major 25 kDa polypeptide and the 14 kDa polypeptide reacted with antibodies against the N-terminal region of TFPI (data not shown). This result suggested that the 14 kDa polypeptide is a proteolytic break-down product of TFPI$_{1\text{-}161}$, possibly consisting of the first Kunitz domain.

As was the case for TFPI$_{1\text{-}161}$ produced in COS-7 cells (copending patent application Ser. No. 07/828,90), TFPI$_{1\text{-}161}$ produced in yeast differed from full length TFPI in its binding characteristics towards heparin. Whereas full length TFPI binds strongly to heparin-Sepharose with about 1M NaCl required for effective elution, TFPI$_{1\text{-}161}$ did not bind to heparin under physiological conditions (0.1M NaCl, 50 mM Tris-HCl, 0.1% BSA, pH 7.4).

Based on weighing of the freeze-dried preparation of purified TFPI$_{1\text{-}161}$ from yeast, a specific activity of 23,000 U/mg in the chromogenic FXa/TF/FVIIa-dependent assay was determined. The activity agrees well with the estimated 30,000 and 10,000 U/mg reported for TFPI isolated from transfected BHK cells (A. H. Pedersen et al., J. Biol. Chem. 265 (1990) 16786–16793) and from the HepG2 hepatoma cell line (Broze, G. J., Jr. et al., Thromb. Res 48 (1987) 253–259).

The anticoagulant activity of purified TFPI$_{1\text{-}161}$ was further analyzed by its ability to inhibit the activity of tissue factor (TF) in direct PT clotting assay where TFPI$_{1\text{-}161}$ was added to the plasma without preincubation with TF. It was found that a concentration of 65 µg/ml of TFPI$_{1-161}$ inhibited 90% of the TF activity. This inhibition was obtained for both high and low concentrations of the TF preparation (thromboplastin).

With full length TFPI from transfected BHK cells only 0.5 µg/ml was required for 90% inhibition of TF activity.

We claim:

1. A recombinant vector capable of directing the expression of a polypeptide analog of Tissue Factor Pathway Inhibitor (TFPI) in yeast, said analog having the amino acid sequence of native TFPI from Asp[1] to Thr[161];

said vector comprising a promoter, a transcription initiation signal, and a terminator operably associated with a nucleic acid sequence which encodes a translation product consisting of a secretion-directing signal peptide concatenated to said TFPI analog.

2. A vector according to claim 1 wherein the encoded signal peptide is selected from the group consisting of the human serum albumin prepropeptide ($pp_{HSA}$) and the synthetic signal sequence 212spx3.

3. A recombinant vector capable of directing the expression of a polypeptide analog of Tissue Factor Pathway Inhibitor (TFPI) in yeast, said vector comprising a promoter, a transcription initiation signal, and a terminator operably associated with a nucleic acid sequence which encodes a translation product consisting of a secretion-directing signal peptide concatenated to said TFPI analog;

the amino acid sequence of said analog differing from the sequence of naturally occurring TFPI by the deletion of the native TFPI sequence from $Gln^{162}$ to $Met^{276}$ and by one or more of the modifications selected from the group consisting of the deletion of one or more additional regions of the native TFPI sequence, the mutation or deletion of one or more of the residues in the $Asn^{117}$-$Gln^{118}$-$Thr^{119}$ triad such that the polypeptide is incapable of being glycosylated at this site in a yeast expression system, and the addition of a Ser residue at the N-terminal of the analog polypeptide; provided that said analog comprises at least the first and second Kunitz domains of native TFPI.

4. A vector according to claim 3 wherein the encoded signal peptide is selected from the group consisting of the human serum albumin prepropeptide ($pp_{HSA}$) and the synthetic sequence 212spx3.

5. A vector according to claim 3 wherein the residue of said analog corresponding to $Asn^{117}$ of native TFPI has been replaced by another amino acid residue.

6. A vector according to claim 5 wherein said residue corresponding to $Asn^{117}$ of native TFPI has been replaced by Gln.

7. A yeast cell transformed with the expression vector of any one of claims 1 to 6.

8. A method of making a TFPI analog, comprising culturing the yeast cell of claim 7 under conditions suitable for the expression and secretion of said analog; and recovering said TFPI analog.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 928 base pairs
        ( B ) TYPE: nucleic acid
        ( C ) STRANDEDNESS: double
        ( D ) TOPOLOGY: linear     ( i i ) MOLECULE TYPE: DNA     ( i i i ) HYPOTHETICAL: NO     ( i v ) ANTI-SENSE: NO     ( v i ) ORIGINAL SOURCE:
        ( A ) ORGANISM: Synthetic     ( i x ) FEATURE:
        ( A ) NAME/KEY: CDS
        ( B ) LOCATION: 8..919

( i x ) FEATURE:
        ( A ) NAME/KEY: sigpeptide
        ( B ) LOCATION: 8..91

( i x ) FEATURE:
        ( A ) NAME/KEY: matpeptide
        ( B ) LOCATION: 92..919

( x i ) SEQUENCE DESCRIPTION: SEQ ID NO:1:

```
GTCGACC ATG ATT TAC ACA ATG AAG AAA GTA CAT GCA CTT TGG GCT AGC        49
        Met Ile Tyr Thr Met Lys Lys Val His Ala Leu Trp Ala Ser
        -28          -25                  -20                  -15

GTA TGC CTG CTG CTT AAT CTT GCC CCT GCC CCT CTT AAT GCT GAT TCT        97
Val Cys Leu Leu Leu Asn Leu Ala Pro Ala Pro Leu Asn Ala Asp Ser
                -10                  -5                           1

GAG GAA GAT GAA GAA CAC ACA ATT ATC ACA GAT ACG GAG CTC CCA CCA       145
Glu Glu Asp Glu Glu His Thr Ile Ile Thr Asp Thr Glu Leu Pro Pro
             5                10                  15

CTG AAA CTT ATG CAT TCA TTT TGT GCA TTC AAG GCG GAT GAT GGG CCC       193
Leu Lys Leu Met His Ser Phe Cys Ala Phe Lys Ala Asp Asp Gly Pro
     20                 25                  30

TGT AAA GCA ATC ATG AAA AGA TTT TTC TTC AAT ATT TTC ACT CGA CAG       241
Cys Lys Ala Ile Met Lys Arg Phe Phe Phe Asn Ile Phe Thr Arg Gln
 35              40                      45                  50

TGC GAA GAA TTT ATA TAT GGG GGA TGT GAA GGA AAT CAG AAT CGA TTT       289
Cys Glu Glu Phe Ile Tyr Gly Gly Cys Glu Gly Asn Gln Asn Arg Phe
                 55                  60                  65

GAA AGT CTG GAA GAG TGC AAA AAA ATG TGT ACA AGA GAT AAT GCA AAC       337
Glu Ser Leu Glu Glu Cys Lys Lys Met Cys Thr Arg Asp Asn Ala Asn
             70                  75                  80

AGG ATT ATA AAG ACA ACA CTG CAG CAA GAA AAG CCA GAT TTC TGC TTT       385
Arg Ile Ile Lys Thr Thr Leu Gln Gln Glu Lys Pro Asp Phe Cys Phe
             85                  90                  95

TTG GAA GAG GAT CCT GGA ATA TGT CGA GGT TAT ATT ACC AGG TAT TTT       433
Leu Glu Glu Asp Pro Gly Ile Cys Arg Gly Tyr Ile Thr Arg Tyr Phe
        100                 105                 110

TAT AAC AAT CAG ACA AAA CAG TGT GAA AGG TTC AAG TAT GGT GGA TGC       481
Tyr Asn Asn Gln Thr Lys Gln Cys Glu Arg Phe Lys Tyr Gly Gly Cys
115                 120                 125                 130
```

```
CTG GGC AAT ATG AAC AAT TTT GAG ACA CTC GAG GAA TGC AAG AAC ATT        529
Leu Gly Asn Met Asn Asn Phe Glu Thr Leu Glu Glu Cys Lys Asn Ile
            135             140                 145

TGT GAA GAT GGT CCG AAT GGT TTC CAG GTG GAT AAT TAT GGT ACC CAG        577
Cys Glu Asp Gly Pro Asn Gly Phe Gln Val Asp Asn Tyr Gly Thr Gln
        150             155                 160

CTC AAT GCT GTT AAC AAC TCC CTG ACT CCG CAA TCA ACC AAG GTT CCC        625
Leu Asn Ala Val Asn Asn Ser Leu Thr Pro Gln Ser Thr Lys Val Pro
        165             170                 175

AGC CTT TTT GAA TTC CAC GGT CCC TCA TGG TGT CTC ACT CCA GCA GAT        673
Ser Leu Phe Glu Phe His Gly Pro Ser Trp Cys Leu Thr Pro Ala Asp
        180             185                 190

AGA GGA TTG TGT CGT GCC AAT GAG AAC AGA TTC TAC TAC AAT TCA GTC        721
Arg Gly Leu Cys Arg Ala Asn Glu Asn Arg Phe Tyr Tyr Asn Ser Val
195             200                 205                 210

ATT GGG AAA TGC CGC CCA TTT AAG TAC TCC GGA TGT GGG GGA AAT GAA        769
Ile Gly Lys Cys Arg Pro Phe Lys Tyr Ser Gly Cys Gly Gly Asn Glu
                215                 220                 225

AAC AAT TTT ACT AGT AAA CAA GAA TGT CTG AGG GCA TGC AAA AAA GGT        817
Asn Asn Phe Thr Ser Lys Gln Glu Cys Leu Arg Ala Cys Lys Lys Gly
            230                 235                 240

TTC ATC CAA AGA ATA TCA AAA GGA GGC CTA ATT AAA ACC AAA AGA AAA        865
Phe Ile Gln Arg Ile Ser Lys Gly Gly Leu Ile Lys Thr Lys Arg Lys
        245                 250                 255

AGA AAG AAG CAG AGA GTG AAA ATA GCA TAT GAA GAA ATT TTT GTT AAA        913
Arg Lys Lys Gln Arg Val Lys Ile Ala Tyr Glu Glu Ile Phe Val Lys
260             265                 270

AAT ATG TGAGTCGAC                                                      928
Asn Met
275
```

( 2 ) INFORMATION FOR SEQ ID NO:2:

( i ) SEQUENCE CHARACTERISTICS:
( A ) LENGTH: 304 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Ile Tyr Thr Met Lys Lys Val His Ala Leu Trp Ala Ser Val Cys
-28             -25                 -20                 -15

Leu Leu Leu Asn Leu Ala Pro Ala Pro Leu Asn Ala Asp Ser Glu Glu
            -10              -5                  1

Asp Glu Glu His Thr Ile Ile Thr Asp Thr Glu Leu Pro Pro Leu Lys
 5              10                  15                  20

Leu Met His Ser Phe Cys Ala Phe Lys Ala Asp Asp Gly Pro Cys Lys
                25                  30                  35

Ala Ile Met Lys Arg Phe Phe Phe Asn Ile Phe Thr Arg Gln Cys Glu
            40                  45                  50

Glu Phe Ile Tyr Gly Gly Cys Glu Gly Asn Gln Asn Arg Phe Glu Ser
        55                  60                  65

Leu Glu Glu Cys Lys Lys Met Cys Thr Arg Asp Asn Ala Asn Arg Ile
    70                  75                  80

Ile Lys Thr Thr Leu Gln Gln Glu Lys Pro Asp Phe Cys Phe Leu Glu
85                  90                  95                  100

Glu Asp Pro Gly Ile Cys Arg Gly Tyr Ile Thr Arg Tyr Phe Tyr Asn
                105                 110                 115

Asn Gln Thr Lys Gln Cys Glu Arg Phe Lys Tyr Gly Gly Cys Leu Gly
            120                 125                 130
```

Asn Met Asn Asn Phe Glu Thr Leu Glu Glu Cys Lys Asn Ile Cys Glu
        135             140             145

Asp Gly Pro Asn Gly Phe Gln Val Asp Asn Tyr Gly Thr Gln Leu Asn
    150             155             160

Ala Val Asn Asn Ser Leu Thr Pro Gln Ser Thr Lys Val Pro Ser Leu
165             170             175             180

Phe Glu Phe His Gly Pro Ser Trp Cys Leu Thr Pro Ala Asp Arg Gly
            185             190             195

Leu Cys Arg Ala Asn Glu Asn Arg Phe Tyr Tyr Asn Ser Val Ile Gly
         200             205             210

Lys Cys Arg Pro Phe Lys Tyr Ser Gly Cys Gly Gly Asn Glu Asn Asn
        215             220             225

Phe Thr Ser Lys Gln Glu Cys Leu Arg Ala Cys Lys Lys Gly Phe Ile
    230             235             240

Gln Arg Ile Ser Lys Gly Gly Leu Ile Lys Thr Lys Arg Lys Arg Lys
245             250             255             260

Lys Gln Arg Val Lys Ile Ala Tyr Glu Glu Ile Phe Val Lys Asn Met
            265             270             275

( 2 ) INFORMATION FOR SEQ ID NO:3:

( i ) SEQUENCE CHARACTERISTICS:
        ( A ) LENGTH: 81 base pairs
        ( B ) TYPE: nucleic acid
        ( C ) STRANDEDNESS: double
        ( D ) TOPOLOGY: linear     ( i i ) MOLECULE TYPE: DNA     ( i i i ) HYPOTHETICAL: NO     ( i v ) ANTI-SENSE: NO     ( v i ) ORIGINAL SOURCE:
        ( A ) ORGANISM: Synthetic     ( i x ) FEATURE:
        ( A ) NAME/KEY: CDS
        ( B ) LOCATION: 1..81

( i x ) FEATURE:
        ( A ) NAME/KEY: miscfeature
        ( B ) LOCATION: 1..54

( i x ) FEATURE:
        ( A ) NAME/KEY: miscfeature
        ( B ) LOCATION: 55..72

( x i ) SEQUENCE DESCRIPTION: SEQ ID NO:3:

ATG AAG TGG GTT ACT TTC ATC TCT TTG TTG TTC TTG TTC TCT TCT GCT    48
Met Lys Trp Val Thr Phe Ile Ser Leu Leu Phe Leu Phe Ser Ser Ala
1               5                       10                  15

TAC TCT AGA GGT GTT TTC AGG AGG GAT TCT GAG    81
Tyr Ser Arg Gly Val Phe Arg Arg Asp Ser Glu
                20                  25

( 2 ) INFORMATION FOR SEQ ID NO:4:

( i ) SEQUENCE CHARACTERISTICS:
        ( A ) LENGTH: 27 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:4:

Met Lys Trp Val Thr Phe Ile Ser Leu Leu Phe Leu Phe Ser Ser Ala
1               5                       10                  15

```
Tyr Ser Arg Gly Val Phe Arg Arg Asp Ser Glu
            20                  25
```

( 2 ) INFORMATION FOR SEQ ID NO:5:

( i ) SEQUENCE CHARACTERISTICS:
        ( A ) LENGTH: 231 base pairs
        ( B ) TYPE: nucleic acid
        ( C ) STRANDEDNESS: double
        ( D ) TOPOLOGY: linear     ( i i ) MOLECULE TYPE: DNA     ( i i i ) HYPOTHETICAL: NO     ( i v ) ANTI-SENSE: NO     ( v i ) ORIGINAL SOURCE:
        ( A ) ORGANISM: Synthetic     ( i x ) FEATURE:
        ( A ) NAME/KEY: CDS
        ( B ) LOCATION: 76..231

( i x ) FEATURE:
        ( A ) NAME/KEY: miscfeature
        ( B ) LOCATION: 76..222

( x i ) SEQUENCE DESCRIPTION: SEQ ID NO:5:

```
GAATTCATTC AAGAATAGTT CAAACAAGAA GATTACAAAC TATCAATTTC ATACACAATA      60

TAAACGATTA AAAGA ATG AAG GCT GTT TTC TTG GTT TTG TCC TTG ATC GGA     111
                 Met Lys Ala Val Phe Leu Val Leu Ser Leu Ile Gly
                  1               5                      10

TTC TGC TGG GCC CAA CCA GTC ACT GGC GAT GAA TCA TCT GTT GAG ATT     159
Phe Cys Trp Ala Gln Pro Val Thr Gly Asp Glu Ser Ser Val Glu Ile
            15                  20                  25

CCG GAA GAG TCT CTG ATC ATC GCT GAA AAC ACC ACT TTG GCT AAC GTC     207
Pro Glu Glu Ser Leu Ile Ile Ala Glu Asn Thr Thr Leu Ala Asn Val
        30                  35                  40

GCC ATG GCT AAG AGA GAT TCT GAG                                      231
Ala Met Ala Lys Arg Asp Ser Glu
45                  50
```

( 2 ) INFORMATION FOR SEQ ID NO:6:

( i ) SEQUENCE CHARACTERISTICS:
        ( A ) LENGTH: 52 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:6:

```
Met Lys Ala Val Phe Leu Val Leu Ser Leu Ile Gly Phe Cys Trp Ala
 1               5                  10                  15

Gln Pro Val Thr Gly Asp Glu Ser Ser Val Glu Ile Pro Glu Glu Ser
            20                  25                  30

Leu Ile Ile Ala Glu Asn Thr Thr Leu Ala Asn Val Ala Met Ala Lys
            35                  40                  45

Arg Asp Ser Glu
50
```